(12) United States Patent
Holsclaw et al.

(10) Patent No.: US 6,482,370 B2
(45) Date of Patent: Nov. 19, 2002

(54) APPARATUS AND METHOD FOR GENERATING AND CIRCULATING OZONE FOR DISINFECTION/STERILIZATION OF DENTAL WATERLINES

(75) Inventors: Ralph L. Holsclaw, Louisville, KY (US); Ray S. Ellis, Jr., New Albany, IN (US)

(73) Assignee: Marco Equipment Distributors, Inc., Louisville, KY (US)

( * ) Notice: Subject to any disclaimer, the term of this patent is extended or adjusted under 35 U.S.C. 154(b) by 47 days.

(21) Appl. No.: 09/771,749

(22) Filed: Jan. 29, 2001

(65) Prior Publication Data

US 2002/0141915 A1 Oct. 3, 2002

(51) Int. Cl.[7] .................................................. B01J 19/08
(52) U.S. Cl. ..................... 422/186.12; 204/176; 433/88; 210/760; 210/764; 210/765
(58) Field of Search ...................... 204/176; 422/186.12; 433/88; 210/760, 764, 765

(56) References Cited

U.S. PATENT DOCUMENTS

| | | |
|---|---|---|
| 3,546,114 A | 12/1970 | Dietz |
| 3,871,913 A | 3/1975 | Shaldon |
| 4,158,034 A | 6/1979 | Riede et al. |
| 4,166,031 A | 8/1979 | Hardy |
| 4,201,664 A | 5/1980 | Hekal |
| 4,444,596 A | 4/1984 | Gortz et al. |
| 4,444,597 A | 4/1984 | Gortz et al. |
| 4,619,763 A | 10/1986 | O'Brien |
| 4,690,772 A | 9/1987 | Tell et al. |
| 4,898,679 A | 2/1990 | Siegel et al. |
| 4,963,331 A | 10/1990 | Mouw |
| 5,078,967 A | 1/1992 | Riera Aixalá |
| 5,173,125 A | 12/1992 | Felding |
| 5,178,830 A | 1/1993 | Riera Aixalá |
| 5,192,459 A | 3/1993 | Tell et al. |
| 5,336,165 A | 8/1994 | Twardowski |
| 5,368,815 A | 11/1994 | Kasting, Jr. et al. |
| 5,370,740 A | 12/1994 | Chao et al. |
| 5,397,397 A | 3/1995 | Awad |
| 5,409,612 A | 4/1995 | Maltais et al. |
| 5,431,861 A | * 7/1995 | Nagahiro et al. .......... 261/36.1 |
| 5,824,243 A | * 10/1998 | Contreras .................. 261/36.1 |
| 5,853,014 A | 12/1998 | Rosenauer |
| 5,942,125 A | * 8/1999 | Engelhard et al. .......... 210/748 |

* cited by examiner

Primary Examiner—Kishor Mayekar
(74) Attorney, Agent, or Firm—Carrithers Law Office; David W. Carrithers

(57) ABSTRACT

The present invention uses ozonated water as a cleaning agent to eliminate bacterial and biofilm in dental water lines instead of using cleaning solutions. The ozonated water disinfects/sterilizes and cleans quickly and without leaving any residue, because the ozone quickly converts to oxygen and goes into the atmosphere. Thus, little or no rinsing is required after using the ozonated water to clean a machine or device. More particularly, the present invention utilizes an apparatus for disinfecting water to make it virtually microbe-free and maintaining it in a continuous microbe-free condition for use at a center for dental applications. Water is ozonated and provided for disinfecting water lines during a cleaning cycle and stored in a pressurized reservoir for use in a variety of dental instruments such as drills, syringes and an expectoration bowl.

7 Claims, 3 Drawing Sheets

APPARATUS AND METHOD FOR GENERATING AND CIRCULATING OZONE FOR DISINFECTION/STERILIZATION OF DENTAL WATERLINES

BACKGROUND OF THE INVENTION

1. Technical Field

The present invention relates to the disinfection/sterilization of dental water lines and the removal of biofilm therefrom and supply of an independent source of disinfected/sterilized water for use in dental offertory applications.

2. Background Information

Tap water in dental offices is similar to drinking water in most public facilities. Although the water is generally considered safe to drink it is not sterile, but contains at least some bacteria counted by CFU/ml, (colony forming units per milliliters).

The water is transferred to the dental offertories through metal or plastic tubing and is supplied to dental handpieces and other dental implements, such as air-water syringes and ultrasonic tooth scalers. Because the water is used at a low flow rate, at infrequent intervals the internal surfaces of the supply lines are ideal for microbial contamination.

As reported by the National Center for the Chronic Disease Prevention and Health Promotion, of the Center for Disease Control, ("CDC"), and set forth in the report published on the Internet under the heading of "Waterborne Infection Control" on Jan. 24, 2001, the problem with water with the quality of the water used in dental applications was reported more than 30 years ago. The reports states that levels of microbial contaimination as high as 10,000 to 10,000,000 CFUs/m.l. have been documented wherein the standard established by the Federal Safe Water Drinking Act for potable water is around 500 CFUs/m.l. of noncoliform bacterial.

Moreover, water that stagnates in plastic water lines and/or tubing overnight and even during long periods during the day provide bacteria the opportunity to stick to the wall of the lines/tubing. Microbial biofilm tends to form along the walls of the long, narow-bore tubing that is used to provide for cooling and irrigating water for dental hand instruments. As set forth in the aforesaid CDC report, microbial biofilm are formed by microorganisms, including bacteria, fungi, and protozoans, that colonize and replicate on the interior surfaces of the waterline tubing formaing a protective slime layer known as a "glycocalyx". Due to the small diameter of the lines, the surface to volume ratio provides an excellent environment for bacterial growth. Moreover, the slow laminar flow rate of the water there through creates an area of laminar flow near the sidewalls of the tubing with very slow flowrates creating stagnant conditions.

The CDC report established that the primary source of the microorganisms is the public water supply. The American dental Association, ("ADA"), has developed a statement on dental unit water lines acknowledging the existence of dental unit water that may be of poor microbiologic quality and has established a goal of limiting the delivery of water to dental patients during nonsurgical procedures of 200 CFUs/m or less. The panels also set forth recommended strategies of prevention including device to monitor water quality, and separate water reservoirs independent of the public water supply, purging water supplies, and inline filters. However, the report goes on to state that none of the methods known appears to permanently eradicate biofilms.

However, the instant invention provides an apparatus and method of use to eradicate dental biofilms and insure a reservoir of disinfected/sterililized water is available for dental applications in an office or laboratory setting, and even as a portable unit for remote locations.

SUMMARY OF THE INVENTION

Most dental unit water lines harbor biofilms that continually shed planktonic organisms as the water is utilized. Many different approaches are being studied to control microbial contamination. Ozone applications to dental unit water line disinfection has been limited. The major drawback appears to be the relative short half-life of ozone, which results in a lack of residual ozone in the water following treatment. The present invention provides a treatment system that reticulates ozonated water through the entire dental unit water line during a cleaning cycle to disinfect/sterilize the lines and provide a source of disinfected/sterilized water to fill a reservoir for use in dental applications in daily operations.

The present invention utilizes an apparatus for disinfecting water to make it virtually microbe-free and maintaining it in a continuous microbe-free condition for use at a center for dental instruments and the other apparatus by ozonated water. Water is ozonated and provided for disinfecting water lines and a variety of dental instruments such as drills, syringes and an expectoration bowl. At least one water reservoir is connected through fluid conduits with such instruments. An ozone producing device is connected with the water reservoir. The ozone level in reservoir or tank is replenished with fresh ozonated water periodically, usually every 24 hours. The freshly ozonated water is utilized to purify the lines and instruments. The remainder of the ozonated water remaining in the reservoir is used throughout the day for dental applications and with dental instruments.

More particularly, in the present invention, an ozone generator provides an outflow of ozone enriched air that is introduced to a water source through a venturi or optionally an ozone air pump or sparger or the like to entrain the ozone enriched air in the water. The ozonated water is conveyed through water lines to each of the various handpieces or water flow dependent implements used by a dentist during the normal course of providing dental services. The ozone introduced into the water will destroy any microbial pathogens in the water and render it essentially microbe free. Furthermore, the living organisms in any biofilm attendant the walls of the water lines will be destroyed upon contact with the ozone. Thus, the water delivered to a patient's oral cavity during the rendering of dental services will be essentially free of any viable microbial activity.

An apparatus for generating ozone and injecting ozone into water and circulating the ozone containing water through dental water lines in a cleaning mode, and providing a source of disinfected/sterlized water for dental applications in an opeation mode includes a reservoir containing water; an ozone generator for for producing ozone; means such as an injector for injecting ozone into the water forming ozonated water; means for pressurizing the reservoir such as with air pressure from a compressor or tank or water pressure such as a city water line; means for depressurging the reservoir such as a relief valve; a pump for recirculating the water from the reservoir through the ozone generator ozonating the water forming ozonate water; an electrical power supply for the ozone generator and the pump recirculating the water; at least one line for circulating the ozonated water to at least one dental offeratory wherein a portion of the ozonated water is used in a dental application and a portion is recirculating to the reservoir; and means such as a timer, rheostat, recorder, and calorimeter for controling the activation of said ozone generator and the amount generated or bacterial content of the water for determining the selected operating intervals and cycle times.

One method method of generating and injecting ozone into water and circulating the ozonated water through dental water lines in a cleaning mode, and providing a source of disinfected/sterlized water for dental applications in an operation mode is as follows:. A cleaning mode comprises the steps of filling a reservoir containing water and opening a pressure relief valve in fluid communication with the reservoir depressurizing the reservoir; activating a power source and an ozone generator producing ozone; activating a pump circulating the water from the reservoir in fluid communication with the ozone generator through an injector in fluid communication with the ozone generator and the reservoir injecting ozone into the water forming ozonated water; and circulating the ozonated water from the reservoir through a water line in fluid communication with at least one dental offeratory for a selected period of time disinfecting/sterilizing the water line and the at least one dental offeatory, and returning the ozonated water from the offeratory to the reservoir in fluid communication with the ozonated water. The same apparatus is used in an operating mode which comprises the steps of deactivating the ozone generator and stopping circulation of the ozonated water for a selected period of time; closing the pressure relief valve in fluid communication with the reservoir for pressurizing same; pressurizing the reservoir and the water line in fluid communication therewith with pressurized air or pressurized water; storing the ozonated water in the reservoir for a selected period of time under pressure providing disinfected/sterilized water in the reservoir and the water lines in fluid communication therewith for use in dental applications.

It is therefore a primary object of the present invention to provide apparatus for delivering water from dental water lines free of any living microbes.

Another object of the present invention is to provide apparatus for destroying any biofilms formed on the walls of water lines.

Yet another object of the present invention is to provide apparatus that delivers to a dental patient water free of microbial activity whether such water be from a municipal water system or a water container.

Still another object of the present invention is to provide apparatus for destroying any microbes present in a dental water line or the water itself each time water flows through the line.

A further object of the present invention is to provide ozonated water to dental handpieces and other dental implements.

A yet further object of the present invention is to provide inexpensive apparatus for ensuring that water delivered to a dental patient is free of living microbes.

A still further object of the present invention is to provide a method for inexpensively and effectively treating and purifying water delivered to dental handpieces.

These and other objects of the present invention will become apparent to those skilled in the art as the claimed invention is described hereafter.

BRIEF DESCRIPTION OF THE DRAWINGS

A better understanding of the present invention will be had upon reference to the following description in conjunction with the accompanying drawings in which like numerals refer to like parts throughout the several views and wherein.

DETAILED DESCRIPTION OF THE PREFERRED EMBODIMENTS

Figure 1:
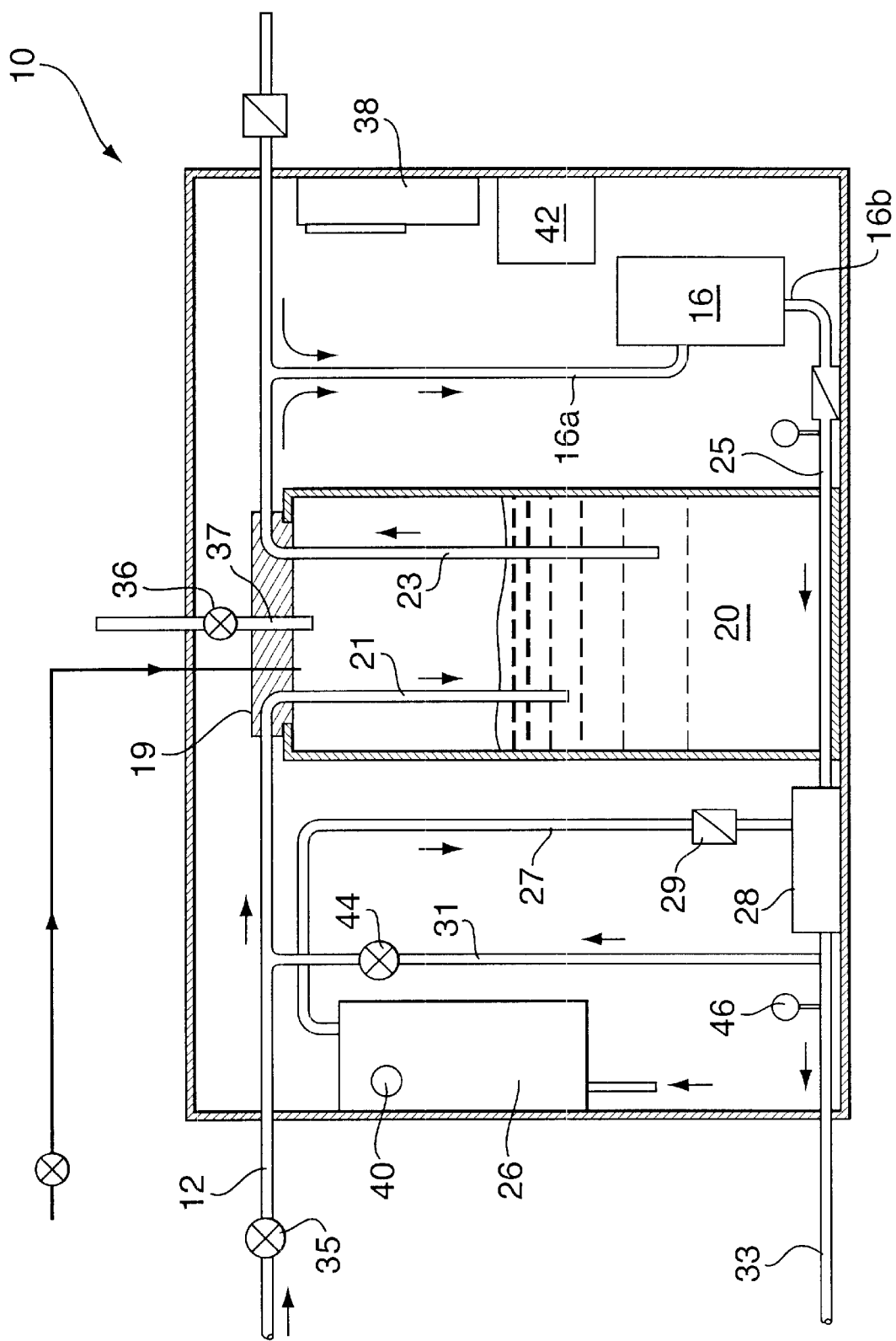
FIG. 1 is a schematic side view of the present invention.

The cleaning apparatus 10 of the present invention is shown in FIG. 1. The apparatus 10 has a water supply line 12, a reservoir tank 20 for holding water, a pump 16 having an inlet side 16a and an outlet side 16b, an ozone generator 26, a venturi injector, and an ozonated water outlet 14. The supply line 12 provides water from the city water supply at standard pressures typically up to 60 psig; however, the preferred embodiment includes a pressure regulator to control the pressure of the water feed supply to about 30 to 40 psig. The city water supply line 12 extends into a cabinet supporting a frame and the water processing apparatus therein. The supply line 12 extends into a cover or lid 19 removably mounted to the top of the reservoir 20. A valve, such as a ball valve, is preferably installed in the supply line 12 and operated manually, or by an air or electric solenoid or other actuator to shut off the water supply flowing to the reservoir 20. The city water flows through the supply line 12 into the reservoir. In a preferred embodiment a length of inlet pipe 21 extending from the supply line 12 protrudes about one-half way to the bottom of the reservoir. A suction pipe 23 extends downward from the top of the reservoir 20 to a depth of about two-thirds of the depth of the reservoir. The suction pipe 23 extends a depth as least as great as the supply line pipe 21. The level of the water within the supply is maintained about the distal ends of the inlet pipe 21 and the suction pipe 23 during the ozonation process. The deeper position of the suction pipe 23 within the reservoir aids in pulling ozonated water from the inlet pipe 23 down into the tank to optimize mixing with the water within the reservoir 20 further promoting uniform mixing of the ozone into the water which is important in view of the tendency of the ozone to dissipate and evolve therefrom as a gas. In one preferred embodiment the supply includes a quick connect coupling (not shown) in order to disconnect the unit from the city water supply to facilitate movement of the unit as a portable unit. A pressure relief valve unit includes a short conduit 37 which extends through the top cover of the reservoir and includes a valve such as a ball valve to release pressure from the reservoir 20 after use for a selected time period.

An ozone generator 26 is mounted to the wall of the cabinet but could be a stand alone unit. The ozone generator 26 may include an air filter to remove contaminants and/or dehumidify the air, and an air flow indicator. The ozone generator 26 converts the oxygen in the air to ozone by passing an electric arc through the air, in a known process. The preferred ozone generator 26 is a 12 volt DC generator and a rheostat 40 for controlling the ozone generation rate. The selected ozone generator 26 yielded an ozone concentration of up to 0.06 ppm ozone in the water or the reservoir 20 and lines in fluid communication therewith as measured by a digital calorimeter. Of course, the instant ozone generator 26 is not limited to a particular voltage and can be modified to run at a different voltage depending upon the available power source. It is contemplated any type of ozone generator 26 should be capable of suppling ozone which is conveyed through the ozone line 27 through a check valve 29 and into the venturi injector 28 to be mixed with the water from the reservoir 20 which may be fresh city water or water mixed with ozonated water. Moreover, a converter 42 may be used to change the 115 Volt AC current to 12 volt DC current depending upon the motor used for the pump or the ozone generator 20. A battery may be substituted for the power supply in order to enhance the portability of the unit. The amount of ozone in the reservoir 20 is dependent upon how long the water is circulated there through the venturi injector 28, and the concentration of ozone if any is in the reservoir 20 prior to starting the ozonation process whereby ozone is pulled through the venturi injector 28 and mixed with water to supply the users as well as to circulate a portion thereof back to the reservoir 20. Although use of the venturi 28 is considered an optimal method for ozonating the water for the instant invention, alternate type of ozonation equipment would work to ozonate the water. A restriction valve 44 is placed within a return line 31 extending from the ozone water product line 33 to the supply line 12 in order to control the flow rate and maintain a desired positive pressure of the ozonated water flowing thorough the small diameter ozoneated water product line 33. A portion of the ozonated water from the injector 28 is allowed to pass the restriction valve 44 to be circulated to the reservoir 20 during use or prior to use and stored within the reservoir 20. Although the ozone will continue to dissipate from the ozonated water within the reservoir after turning off the pump 16 and ozone generator 26, the ozonated water in the reservoir 20 will remain disinfected/sterile unless contaminated. Moreover, the concentration of the ozone can be increased by utilizing a oxygen enriched air as the ozone air feed supply instead of ambient air. A check valve 29 is not required, but recommended to be placed between the ozone generator and the venturi injector 26 to prevent blow back of water into the ozone generator 20. The ozonation cleaning cycle mode process is repeated at selected time intervals, such as every night, to ensure an adequate supply of sterile water to the dental equipment during the daily operational mode use.

Moreover, the pump 16 pulls water from the reservoir 20 thorough the suction line 23 and discharges the reservoir water through a transfer line 25 forcing the fluid thorough a venturi injector 28 in the product line 33 connected to the ozone supply line 27.

The water inlet valve 35 and pressure relief valve 36 may be opened and closed manually, or a timer 38 can be used to active the solenoids to open the city water inlet valve 35 and close the pressure relief valve 36 for filling the reservoir 20 and pressurzing the system. After the inlet feed valve 35 to the reservoir 20 is closed and the relieve valve 36 opened, means for controlling the activation of the pump and ozone generator such as the timer 38 is used to activate the pump and ozone generator to recirculate the water to be ozonated and/or previously ozonated water through the venturi injector 28 to disinfect and/or sterilize the water in the reservoir and product supply lines and product return line. A means for indicating such as a float or sight glass may be used in place of or together with the timer 38 to control the amount of water in the reservoir 20. Moreover, a rotameter may be used to measure the flowrate of the water in the lines. A counter or a recorder may also be utilized to count or record the time the pump and/or ozone generator has been activated. Moreover, the data may be feed to a microprocessor or computer and be available for review on a terminal or accessed via a telephone line.

All of the controls and indicators can be centralized by use of a control panel with activation and deactivation switches, pressure gauges, and indicator lights and/or alarms. A sensor may also indicate the amount of water within the reservoir. Moreover, an ORP, "Oxidation Reduction Potential" sensor and optionally recorder may be used to monitor the amount of ozone in the reservoir water or ozone feed line. Other means to read ozone concentration such as a digital calorimeter can be used in combination with the treatment system. An on/off switch may also be incorporated into the control panel. One or more indicator lights may be incorporated within a process flow diagram to indicate the location of the sites utilizing the ozonated water product.

METHOD OF USE

The inlet feed valve in the supply line is opened and the relief valve to the reservoir 20 is closed and the city water or water from an alternate supply source such as a feed tank is feed through the regulator under pressure to the reservoir 20 through line 21. Then the inlet feed valve is closed and the pressure relief valve is opened. The timer is activated which activates the pump, ozone generator, and counter/recorder. The pump 16 pulls water by suction through line 23 from the reservoir 20 and pumps the water through line 25 and through the venturi injector 26. The ozone generated is sucked into the venturi and injected into the water stream thereby ozonating the water. The ozonated water product is pumped through a small diameter ozonated water supply line to the dental equipment and returned through a small diameter line to a tee and is sucked back through the pump and/or returns to the tank through the suction line 23 if the pump is not activated. Moreover, the line carrying the ozonated water product from the venturi injector includes a tee whereby water not flowing through the small diameter ozonated water supply line is returned to the reservoir through a by-pass line. A means for restricting the flow through the by-pass line such as a restriction valve 44, which can be a manually set ball valve or possibly an electrically/air operated adjustable valve, controls the pressure and quantity of the ozonated water product through the small diameter line to maintain predetermined amount of ozonated water product flowing through the small diameter ozonated water product line to the dental equipment.

A pressure gauge 46 may be used to monitor the pressure of the water flowing through the small ozonated water product line to ensure that the pressure of the water is maintained in a selected range to insure and adequate supply at a selected pressure range through the lines feeding the dental equipment.

Cleaning/Disinfection/Sterilization Mode

In one preferred embodiment, after the ozonated water product has flowed through the dental lines and equipment for a predetermined period of time the timer shuts off the pump, ozone generator, and counter/recorder for a selected period of time. This off-on cycle can be repeated at predetermined intervals as needed to disinfect or sterilize the lines and equipment and remove any biofilm buildup that may be present in the lines by using the ozonated water. For instance, the on cycle may be of a duration of, for example 30 minutes, and the off cycle may be of a duration of for instance, 45 minutes. The on cycle may be set to run continuously; however, it may not be necessary to run the ozone generator continuously or for extended periods of time once the disinfection or sterilization of the lines has been achieved, because intermittent circulation of the ozonated water product serves to maintain the lines, and equipment at an acceptable level of disinfection. The cleaning/disinfection/sterilization mode is typically performed after normal dental/business hours, "at night". In this recirculating mode, the relief valve is open and the reservoir is not pressurized. The pump provides pressure for recirculating the ozonated water product through the lines and the reservoir.

During the cleaning mode, the small diameter ozonated water product line carries the treated water to various types of dental hand pieces such as drills, air water syringes, chippers, polishing devices, and all other devices requiring the use of water. The ozonated water product line may have one or more tees or "Y"s to transfer the product to the various treatment points "hand pieces". A means for recirculating the ozonated water product such as a tee or recirculating valve is installed immediately prior to entering the hand piece, and the ozonated water is recirculated thorough the return line to the reservoir through the line adjoining the pump and suction lines of the instant invention. More particularly, the means for recirculating may define a tee fitting, or a recirculating valve body such as set forth in FIG. 2, whereby a syringe connector block includes a inlet tube and two outlet tubes in order for the water to penetrate the lines as deep as possible up to the abutment of the hand piece connection to the line. The penetration of the ozonated water product to the furthest point possible is a critical consideration in treating and controlling biofilm and disinfecting/sterilizing the aqueous environment.

The ozonated water product line may include a plurality of branch lines or capillary lines feeding various hand pieces at a given offertory. The return line may also serve as the feed line for multiple offertories with the return line from the last offertory in the series returning the ozonated water to the reservoir or to the suction line feeding the pump. An alternate arrangement involves using a manifold branching off of the ozonated water product line at each offertory and a manifold to receive the various return lines from each one of the offertories which conveys the ozonated water to the suction line from the reservoir feeding the pump. Of course, the ozonated water could be returned directly to the reservoir through a separate designated line.

Operation Mode

After circulation of the ozonated water product has accomplished the task of cleaning and disinfecting/sterlizing the water lines and dental apparatus. The pump, ozone generator, and counter/recorder are turned off, and the inlet water valve is turned on. The relief valve is closed and the water feed supply line 12 valve is open to pressurize the system including the ozonated water product remaining in the reservoir and lines. Within a short period of time typically about thirty minutes the ozone dissipates and returns to its original state of oxygen "$O_2$". An alternate means for pressurizing the system is to use air to pressurize the system instead of water, by for instance, injecting air through a line into the cover of the reservoir 20. Air pressure could also be used to maintain the pressure in the system during the operation or "in use period" during the day rather than water pressure. Of course, upon opening the air pressure valve, the water inlet supply valve should be in the closed position, and the air valve closed before opening the water inlet supply valve to refill the tank. The water inlet supply valve is closed and the relief valve opened before repeating the cleaning mode.

Over a period of time the ozone will dissipate from the ozonated water product leaving no residual ozone in the water system and return to its original state of oxygen. However, the water remaining in the reservoir and in the lines will be remain disinfected or sterile and is ready for use by the dentist as an available source of disinfected or sterile water supply for dental applications.

Thus, the instant invention provides a means of cleaning, disinfecting or sterilizing dental equipment and lines and removing biofilm therefrom, and the same ozonated water product provides an independent source of disinfected/sterile water for dental applications.

Since the ozone in the enclosed pathway is protected from contact with the atmosphere, the ozone gas tends to stay in solution in the water during the time the ozonated water is being pumped through the enclosed pathway during the cleaning mode. After disinfecting the dental water lines and instruments connected thereto any ozone remaining in the reservoir dissipates to the atmosphere, leaving no contaminants in the reservoir and an ample supply of disinfected/sterilized water for use during the day for use with dental equipment and for the needs of the patients. Thus, once the flow of ozonated water has disinfected and purged the lines, it is followed by a flow of disinfected/sterile water.

EXPERIMENTAL EVALUATION AND RESULTS

Experimental testing was conducted using the above-described equipment and methods of operation. Samples were collected and analyzed by the University of Louisville Dental School in Louisville, Ky. The results were presented in an Abstract which is being submitted by the University of Louisville School of Dentistry in Louisville, Ky, USA, for publication in one or more dental journals entitled "Continuous Ozone Treatment a Means to Control dental Unit Waterline Biofilms" by B. E. Cardon, P. Eleazer, P. A. Shepherd, and R. H. Staat and is hereby incorporated by reference.

EXPERIMENT 1

For the experiment, water was collected from two water lines, (untreated water lines 1 and 2), of untreated dental units which had been in service for at least 5 years. These lines were preserved in their original condition to prevent desiccation of the accumulated biofilm and provide test samples.

In the instant experiment, for both the control and treatment cycles, a series of water samples were collected in sterile containers at various times. All samples were taken directly to a laboratory for analysis. Each water sample was mixed thoroughly with a vortex mixer and 0.10 ml was plated onto R2A medium for total CFU determination. Plated samples were incubated at 30° C. for 5 days. Colonies were counted manually using a light microscope.

Water line 1 was connected to the ozone treatment apparatus and before the ozone generator was turned on. The pump was run for 30 minutes without ozonation to provide a control cycle or a baseline water sample to measure the bacteria content, CFU/ml, from the system's water. The water in the treatment system, (lines or reservoir) contained 920 CFU/ml 0.0 ppm ozone before turning the system on.

After installation of water line #1, a baseline sample from the end of the line had 2.4×10³ CFU/ml and 0.0 ppm ozone. A control sample taken at the end of the line after thirty minutes of running the system without ozone added to the water had 2.8×10⁴ CFU/ml and 0.0 ppm ozone.

After one minute of ozone addition, colony counts from the end of water line 1 had diminished to 920 CFU/ml. After 10 minutes, the count was 110 CFU/ml. Thereafter, 20, 30, 45 and 60 minute samples were taken which yielded 90, 40, 10 and 10 CFU/ml respectively as set forth in Table 1 below and FIG. 1. Furthermore, after one week of performing 3 or 4 cleaning cycles per day of ozone maintenance treatment, the water contained 0 CFU.

In a prior test run of the apparatus described heretofore, treatment cleaning cycles were run using water which yielded an ozone concentration of up to 0.06 ppm ozone as measured by a digital colorimeter.

TABLE 1

| Time (minutes) | 0 | 1 | 10 | 20 | 30 | 45 | 60 |
|---|---|---|---|---|---|---|---|
| CFU/ml | 28,500 | 720 | 110 | 90 | 40 | 10 | 10 |

Table 1 shows the decline in CU/ml when water containing 0.06 ppm ozone is flushed through Water line No. 1 taken from a dental unit with five years of use.

EXPERIMENT 2

The experimental procedure as set forth in Experiment 1 was repeated on a separate day using untreated water line #2 under the same conditions and running the same sequence, only without a 30 minute nonozonated cycle.

Figure 2:
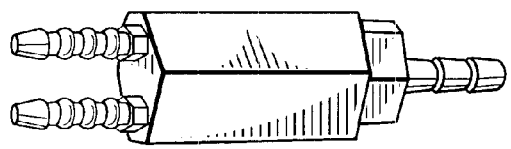
FIG. 2 is a perspective view of a recirculating body valve which can be used with the present invention.

Similar results to those obtained in the first experiment were obtained using waterline #2 as set forth in Table 2 and FIG. 2.

TABLE 2

| Time (minutes) | 0 | 1 | 5 | 15 | 25 | 35 |
|---|---|---|---|---|---|---|
| CFU/ml | 3400 | 800 | 240 | 120 | 70 | 70 |

Table 2 shows the decline in CU/ml when water containing 0.06 ppm ozone is flushed through Water line No. 2 taken from a dental unit with five years of use.

EXPERIMENT 3

The experimental procedure as set forth in Experiment 2 was repeated on a separate day wherein a cleaned water line was used to run a third test in which highly contaminated water was added to the system before ozone treatment.

Figure 3:
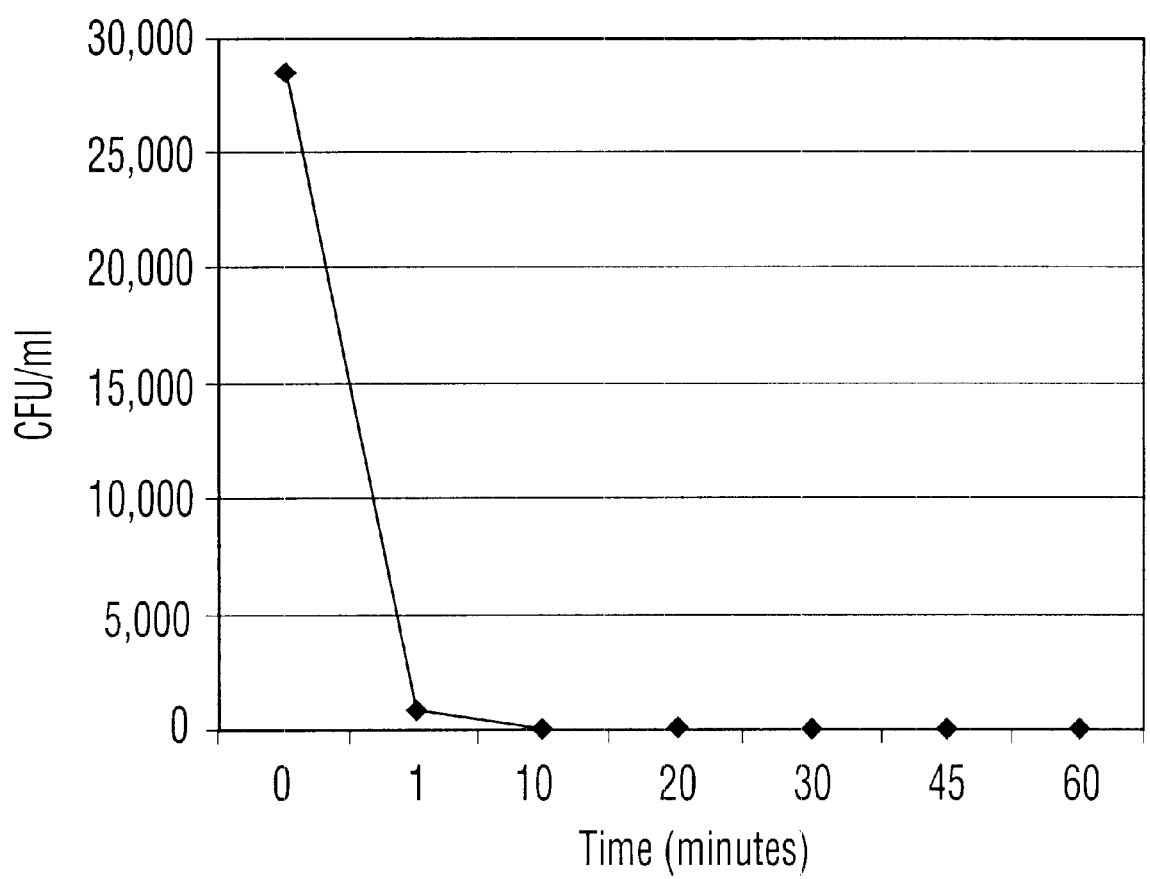
FIG. 3 is a graph showing the decline in CU/ml when water containing 0.06 ppm ozone is flushed through Water line No. 1 taken from a dental unit with five years of use.
Figure 4:
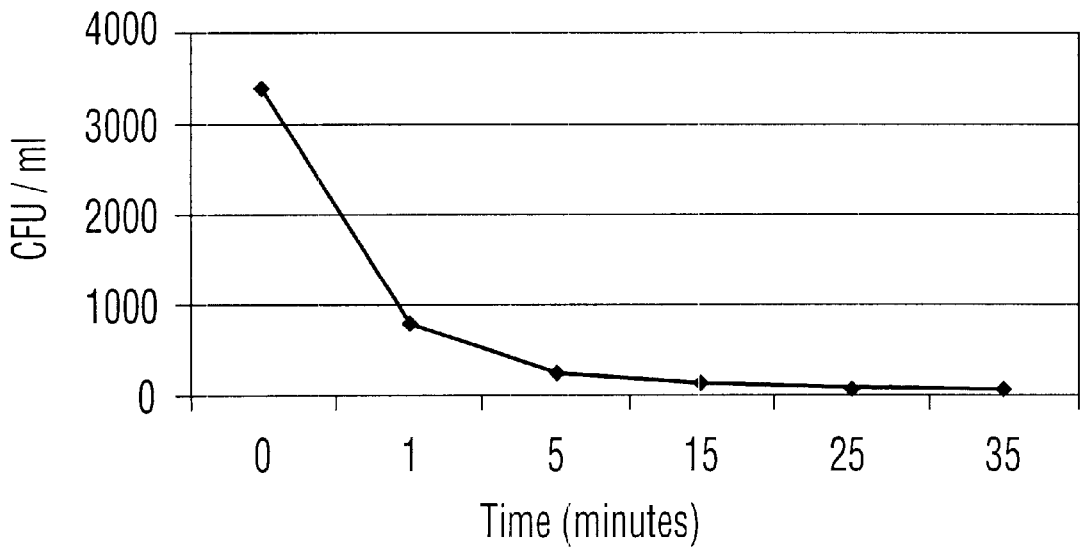
FIG. 4 is a graph showing the decline in CU/ml when water containing 0.06 ppm ozone is flushed through Water line No. 2 taken from a dental unit with five years of use.
Figure 5:
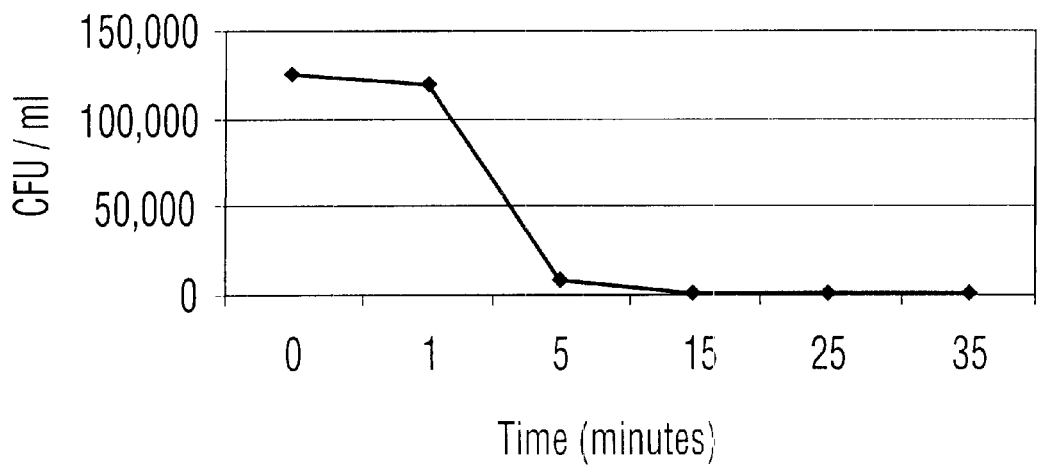
FIG. 5 is a graph showing the decline in CU/ml when water containing 0.06 ppm ozone is flushed through a water line contaminated with water containing $1.2 \times 10^5$ CFU/ml when treated with 0.06 ppm ozone.

The third trial using highly contaminated water showed that after 35 minutes of ozone treatment, the count had diminished from a count of 1.2×10⁵ CFU/ml to a count of 410 CFU/ml as set forth in Table 3 and FIG. 3.

TABLE 3

| Time (minutes) | 0 | 1 | 5 | 15 | 25 | 35 |
|---|---|---|---|---|---|---|
| CFU/ml | 126000 | 120000 | 8400 | 900 | 520 | 410 |

Table 5 shows the decline in CU/ml when water containing 0.06 ppm ozone is flushed through a water line contaminated with water containing 1.2×10⁵ CFU/ml when treated with 0.06 ppm ozone.

In conclusion, waterlines from an untreated dental unit that had been in use for at least 5 years were connected to the apparatus for generating ozone through the dental water lines and providing an independent source of disinfected/sterile water as described heretofore. The water was ozonated to obtain recirculating water contained 0.06 ppm ozone. Water samples were taken from the recirculating system at various times and plated on R2A agar medium for total CFU determinations. An analysis of the results revealed that the total CFU count had dropped from 2×10⁴ to 1.1×10² after 10 minutes of ozone treatment, and after a total of 45 minutes of recirculating, the CFU count was further reduced to only 10 colonies. Further ozone treatment utilizing three or four cleaning cycles per day in the manner as set forth above for one week maintained the count at 0 CFU. The results indicate that systematic cycling of ozonated water through dental unit water lines is capable of controlling accumulation of associated biofilms.

The foregoing detailed description is given primarily for clearness of understanding and no unnecessary limitations are to be understood therefrom, for modifications will become obvious to those skilled in the art based upon more recent disclosures and may be made without departing from the spirit of the invention and scope of the appended claims.

We claim:

1. An apparatus for generating ozone and injecting ozone into water and circulating the ozone containing water through dental water lines in a cleaning mode, and providing a source of disinfected/sterlized water for dental applications in an opeation mode, comprising:

a reservoir for containing water;

an ozone generator for producing ozone;

means for injecting ozone into said water forming ozonated water;

means for pressurizing said reservoir;

means for depressuring said reservoir;

a pump for recirculating said water from said reservoir through said means for injecting ozone;

a power supply for said ozone generator and said pump;

at least one line for circulating said ozonated water to at least one dental of feratory wherein a portion of said ozonated water is used in a dental application and a portion is recirculating to said reservoir; and means for controlling the activation of said ozone generator and said pump for selected operating intervals at selected periods of cycle times.

2. The apparatus of claim 1, including a source of compressed air in fluid communication with said reservoir.

3. The apparatus of claim 2, wherein said means for pressurizing said reservoir is compressed air.

4. The apparatus of claim 1, including a source of pressurized water in fluid communication with said reservoir.

5. The apparatus of claim 4, wherein said means for pressurizing said reservoir is pressurized water.

6. The apparatus of claim 1, wherein said means of injecting ozone into said water is an injector.

7. A method of generating and injecting ozone into water and circulating ozonated water through dental water lines in a cleaning mode, and providing a source of disinfected/sterlized water for dental applications in an operation mode, comprising:

1) a cleaning mode comprising the steps of:
   filling a reservoir containing water and opening a pressure relief valve in fluid communication with said reservoir depressurizing said reservoir;
   activating a power source and an ozone generator producing ozone;
   activating a pump circulating said water from said reservoir in fluid communication with said ozone generator through an injector in fluid communication with said ozone generator and said reservoir injecting ozone into said water forming ozonated water;
   circulating said ozonated water from said reservoir through a water line in fluid communication with at least one dental offeratory for a selected period of time disinfecting/sterilizing said water line and said at least one dental offeratory, and returning said ozonated water from said offeratory to said reservoir in fluid communication with said ozonated water; and
2) an operating mode comprising the steps of:
   deactivating said ozone generator and stopping circulation of said ozonated water for a selected period of time;
   closing said pressure relief valve in fluid communication with said reservoir;
   pressurizing said reservoir and said water line in fluid communication therewith with pressurized air or pressurized water;
   storing said ozonated water in said reservoir for a selected period of time under pressure providing disinfected/sterilized water in said reservoir and said water lines in fluid communication therewith for use in dental applications.

* * * * *